(12) United States Patent  
Calder

(10) Patent No.: US 12,115,038 B2  
(45) Date of Patent: Oct. 15, 2024

(54) RELATING TO, APPLICATORS

(71) Applicant: Simcro Limited, Hamilton (NZ)

(72) Inventor: David Bain Calder, Ohaupo (NZ)

(73) Assignee: Datamars SA, Lamone (CH)

( * ) Notice: Subject to any disclaimer, the term of this patent is extended or adjusted under 35 U.S.C. 154(b) by 869 days.

(21) Appl. No.: 16/972,587

(22) PCT Filed: Jun. 6, 2019

(86) PCT No.: PCT/NZ2019/050066  
§ 371 (c)(1),  
(2) Date: Dec. 5, 2020

(87) PCT Pub. No.: WO2019/235942  
PCT Pub. Date: Dec. 12, 2019

(65) Prior Publication Data  
US 2021/0236255 A1  Aug. 5, 2021

Related U.S. Application Data

(60) Provisional application No. 62/681,653, filed on Jun. 6, 2018.

(51) Int. Cl.  
*A61D 7/00* (2006.01)  
*A61M 5/31* (2006.01)  
*A61M 5/315* (2006.01)

(52) U.S. Cl.  
CPC ....... *A61D 7/00* (2013.01); *A61M 2005/3128* (2013.01); *A61M 5/315* (2013.01); *A61M 2250/00* (2013.01)

(58) Field of Classification Search  
CPC . A61D 7/00; A61M 5/14216; A61M 5/31581; A61M 2005/3114;  
(Continued)

(56) References Cited

U.S. PATENT DOCUMENTS 4,245,757 A * 1/1981 Phillips .................... A61D 7/00  
222/43  
9,950,855 B1 * 4/2018 Holland ............ A61M 5/31501  
(Continued)

FOREIGN PATENT DOCUMENTS

WO   WO2008122018 A1   10/2008  
WO   WO2008143529 A2   11/2008  
(Continued)

*Primary Examiner* — Nathan R Price  
*Assistant Examiner* — Kayla M. Turkowski  
(74) *Attorney, Agent, or Firm* — Lowe Graham Jones PLLC

(57) ABSTRACT

Disclosed is an applicator, and a handle for an applicator. The applicator has at least one barrel and a piston moveable within the at least one barrel to stroke between a variable first position and a second position. In use, movement of the piston towards the first position can draw a first fluid into the barrel, and movement of the piston towards the second position can force the first fluid out of the barrel. The barrel has at least one fluid inlet valve to allow the fluid to flow into the at least one barrel at least under action of the piston, and at least one fluid outlet valve to allow the first fluid to flow out of the at least one barrel at least under action of the piston. A handle has a piston actuator assembly, housed at least in part within a body of the handle, operable to move the piston towards the second position to dispense the first fluid from the applicator. The piston actuator has a first actuating component driven by a user operated handle to pivot and tension a first biasing component, a second actuating component held in position against a force of the first biasing component, a first trigger component that holds the second actuating component in place until a required force is reached by the first biasing component, or a second trigger component releases the first trigger component. The second actuating component is then released and driven by the force of the first biasing component to in turn drive the piston (Continued)

toward the second position. The movement of the first actuating component is independent of the stroke of the piston.

15 Claims, 14 Drawing Sheets

(58) Field of Classification Search
CPC ............ A61M 2250/00; A61M 5/1424; A61M 5/31593; A61M 5/31595; A61M 5/204
USPC .......................................................... 604/71
See application file for complete search history.

(56) References Cited

U.S. PATENT DOCUMENTS

| | | | |
|---|---|---|---|
| 2008/0147005 A1* | 6/2008 | Moller | A61M 5/31583 604/134 |
| 2010/0199984 A1* | 8/2010 | Williams, III | B05B 11/0032 128/200.23 |
| 2013/0345659 A1* | 12/2013 | Shay | A61M 5/1424 604/500 |
| 2017/0000594 A1* | 1/2017 | Buckley | A61D 1/02 222/43 |
| 2017/0296753 A1 | 10/2017 | Rowe et al. | |
| 2018/0110929 A1* | 4/2018 | Vivien | A61M 5/20 |
| 2019/0022315 A1* | 1/2019 | Udy | A61M 5/315 |
| 2019/0183622 A1* | 6/2019 | Halamish | A61M 39/24 |
| 2021/0077729 A1* | 3/2021 | Altermann | A61M 5/30 |
| 2021/0228806 A1* | 7/2021 | Streeter | A61M 5/1782 |

FOREIGN PATENT DOCUMENTS

| | | |
|---|---|---|
| WO | WO2015101981 A1 | 7/2015 |
| WO | WO2016138018 A2 | 9/2016 |

\* cited by examiner

RELATING TO, APPLICATORS

TECHNICAL FIELD OF THE INVENTION

The present invention relates to applicators for fluids and the like.

In particular, though not solely, the present invention is directed to applicators for animals to apply a fluid orally, nasally, topically or subcutaneously to the animal.

BACKGROUND OF THE INVENTION

Animal remedies for sheep, cattle, goats, llama and the like farmed animals for veterinary and/or animal husbandry are applied by a number of methods including topical or "pour-on" application, oral application, injection, including subcutaneous, and nasal infusion. Each of these is typically dispensed from a "pistol grip" style dispenser or applicator.

Typically such applicators have a piston or plunger which can be reciprocated within a barrel by squeezing and releasing a first handle relative to a second handle. The liquid to be dispensed is drawn into the barrel through an inlet via a one way inlet valve when the plunger is withdrawn inside the barrel, and is dispensed through a nozzle via an outlet valve when the plunger is extended towards the outlet valve. The inlet, barrel, piston and outlet are typically inline. The movement of the handles moves the piston along this line.

As is described above, conventional fluid applicators incorporate two one-way valves. These valves are referred to as the inlet valve and the outlet valve.

The valves are typically biased with springs, so that they open only when there is a predefined difference in the fluid pressure between the upstream side of the valve and the downstream side. Fluid cannot flow backwards through either valve under normal operating conditions, as flow in this direction will tend to push the valves more tightly closed.

When the applicator is at rest, both valves are closed. When the applicator is in use, it is intended that only one valve opens at a time. During the discharge stroke, the outlet valve is pushed open by the raised fluid pressure within the barrel. During the refill stroke, the inlet valve is pushed open by fluid entering the barrel (where there is now a partial vacuum).

Such an applicator is described in the applicant's New Zealand patent NZ 521084, the contents of which are herein incorporated by reference. The applicator in NZ 521084 typifies the pistol grip form applicator and is one of the shapes and lay outs for such applicators.

One short coming of the current shape applicators in the in line nature of the components. The applicator has an inlet, inlet valving, barrel with piston, outlet valving, and applicator, typically all in line above the actuating handles. This makes the applicator quite long. In modern farming practices it is important that the applicator be as compact as possible so as to be easy to use and manoeuvre in tight environments such as through gaps in a stock chute, or when moving through a herd of animals. Long, potentially delicate applicators of the prior art can get hung up on fences, chutes, animals and the like, and may require more than one hand to locate and operate. This can cause fatigue for the user, and lengthen the time for each applied dose.

A further requirement is to reduce the fatigue of the user, when actuating the applicator to deliver the dose, especially when treating a large number of animals. The dose of most actuators can be adjusted. One way this adjustment is typically done is to limit the start or stop position of the piston's movement in the barrel, that is, its withdrawn position, or its extended position respectively. This method is useful because it is simple and straight forward to implement and is reliable. NZ521084 describes a mechanism comprising a cylindrical dosage control part which is provided with a plurality of stopping ribs, each of a different length. Rotation of the dosage control part allows selection of which of the stopping ribs is engaged by a rib provided on the plunger, and therefor allows adjustment of the maximum stroke of the plunger.

Notably, the dosage control part encircles the plunger, and so the plunger must be of adequate length to allow the plunger to achieve its full or stroke (dependent on the setting of the dosage control part) before the mechanism which actuates the plunger comes into contact with the dosage control part.

In this way the one applicator can be used for a variety of doses, for example depending on animal weight at the time, or over time.

However, the moving handle is directly connected to the piston. Therefore whichever position of the piston that is limited results in a shortened stroke of the two handles relative to each other. For example, when a minimal dose is supplied from the applicator the handle stroke is very small. This results in a very small movement of the hand for the user. In contrast the largest dose the applicator can deliver will result in full movement of the two handles relative to each other. Whichever position the handle is in, short stroke for a small dose, or long stroke for maximum dose the user must still overcome the stiction of the piston in the barrel, and the opening pressure required to actuate the valves, for example the outlet valve to deliver the dose, or vice versa. The best leverage for the user to easily exert this required force on the handles is at or near the full movement of the handles. Therefore a user's hand leverage is compromised when the handles are nearly closed for the smallest dose delivery, yet the user must still overcome this starting force to deliver the dose. This can lead to increased time to dose, fatigue over the short to medium term, and repetitive injury over the long term.

When the applicator is used in the veterinary and/or animal husbandry fields it should preferably have the following characteristics: be simple and reliable, suited to use in an agricultural environment.

be inexpensive to implement.

not interfere with the dose accuracy of the applicator.

work regardless of the height of the fluid source relative to the applicator.

work regardless of the viscosity of the fluid.

work regardless of the speed of discharge or refill.

work correctly during all stages of the applicator's operating cycle, including discharge, refill, and unexpected pauses in mid-stroke.

withstand attack by aggressive chemicals.

Applicators may also require periodic servicing of various inlet and outlet valves in order to stay in good working condition. It is desirable for this servicing to be achievable as quickly and simply as possible. However, many applicators of the prior art have inlet and outlet valves located at a plurality of locations, or require disassembly of parts that do not need servicing to access the areas that need service. Therefore they require significant disassembly of the applicator for the valves and the like to be serviced.

Such applicators also are typically unitary in that failure in one part of the applicator leads to the entire applicator being replaced as typically spare parts are not available or provided. Worse, if an applicator is attempted to be repaired, for example using non-specific parts, then the applicator may not operate accurately, or as intended.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

It is an object of the present invention to provide an improved applicator, or to overcome the problem of handle movement changing with the dose selected, or to overcome the above shortcomings or address the above desiderata, or to at least provide the public with a useful choice.

BRIEF DESCRIPTION OF THE INVENTION

In a first aspect the present invention consists in an applicator comprising or including, at least one barrel;
 a piston moveable within the at least one barrel to stroke between a variable first position and a second position, wherein, in use, movement of the piston towards the first position can draw a first fluid into the barrel, and movement of the piston towards the second position can force the first fluid out of the barrel;
 at least one fluid inlet valve to allow the fluid to flow into the at least one barrel at least under action of the piston, and at least one fluid outlet valve to allow the first fluid to flow out of the at least one barrel at least under action of the piston;
 a piston actuator assembly, housed at least in part within a body, operable to move the piston towards the second position to dispense the first fluid from the applicator, wherein the piston actuator comprises a first actuating component driven by a user operated handle to pivot and tension a first biasing component, a second actuating component held in position against a force of the first biasing component, a first trigger component that holds the second actuating component in place until a required force is reached by the first biasing component, or a second trigger component releases the first trigger component, whereby the second actuating component is then released and driven by the force of the first biasing component to in turn drive the piston toward the second position,
 and wherein the movement of the first actuating component is independent of the stroke of the piston.

Preferably the piston and barrel are not in line with the first and second actuating means, but rather are at an angle to them, or a main axis of the applicator.

Preferably the stroke of the piston is at or near vertical when the applicator is held normally.

Preferably a handle component extends from the body and the user operated handle pivots from a first pivot point at a distal end of the handle component.

Preferably the user operated handle is driven to extend away from the handle component by a second biasing component.

Preferably the first trigger component is biased to hold the second actuating component in place until that biasing force is overcome by the force of the first biasing component, or by the second trigger component.

Preferably the first actuating component and second actuating component are pivotally mounted on the housing from a common second pivot point.

Preferably the second trigger component is a sliding sheath that slides in line with the main axis, and has a trigger portion that releases the first trigger component.

Preferably the second trigger component is biased away from the first trigger component.

Preferably the first trigger component is pivotally mounted from the housing.

Preferably there is a locking portion that locks to prevent movement of the piston actuator.

Preferably the locking portion prevents or allows movement of the second trigger component.

Preferably the locking portion extends about the second trigger component.

Preferably the locking portion is rotating locking barrel to rotate in a first direction and prevent movement of the piston actuator, and to rotate in a second direction to allow movement of the piston actuator.

Preferably the barrel is replaceable to vary the dose of the applicator.

Alternatively the barrel can receive an insert to provide a stop of the second position of the piston to vary the dose of the applicator.

Alternatively the barrel has a variable stop to vary the second position of the piston to vary the dose of the applicator.

Preferably the inlet valve, applicator, outlet valve, piston and barrel can be removed as an dose assembly from the body.

In a second aspect the present invention consists in an applicator to dispense a fluid or the like, comprising or including,
 at least one barrel;
 a piston moveable within the at least one barrel to stroke between a variable first position and a second position, wherein, in use, movement of the piston towards the first position can draw a first fluid into the barrel, and movement of the piston towards the second position can force the first fluid out of the barrel;
 at least one fluid inlet valve to allow the fluid to flow into the at least one barrel at least under action of the piston, and at least one fluid outlet valve to allow the first fluid to flow out of the at least one barrel at least under action of the piston;
 a piston actuator assembly, housed at least in part within a body, operable to move the piston towards the second position to dispense the first fluid from the applicator, wherein the piston actuator comprises
 a first actuating component driven by a user operated handle to pivot and tension a first biasing component, wherein the first biasing component in turn provides a force against a second actuating component until the second actuating component is released to in turn drive the piston towards the second position and thence dispense the fluid, and wherein the movement of the first actuating component is independent of the stroke of the piston.

Preferably there is a second actuating component held in position against the force of the first biasing component, a first trigger component that holds the second actuating component in place until a required force is reached by the first biasing component, or a second trigger component releases the first trigger component, whereby the second actuating component is then released and driven by the force of the first biasing component to in turn drive the piston toward the second position.

In another aspect the present invention consists in a handle for an applicator, the handle adapted to move at least one piston in at least one barrel, to stroke between a variable first position and a second position, wherein, in use, movement of the piston towards the first position can draw a first fluid into the barrel, and movement of the piston towards the second position can force the first fluid out of the barrel; the barrel having at least one fluid inlet valve to allow the fluid to flow into the at least one barrel at least under action of the piston, and at least one fluid outlet valve to allow the first fluid to flow out of the at least one barrel at least under action of the piston;

the handle comprising,
   a piston actuator assembly, housed at least in part within a body, operable to move the piston towards the second position to dispense the first fluid from the applicator, wherein the piston actuator comprises a first actuating component driven by a user operated handle to pivot and tension a first biasing component, a second actuating component held in position against a force of the first biasing component, a first trigger component that holds the second actuating component in place until a required force is reached by the first biasing component, or a second trigger component releases the first trigger component, whereby the second actuating component is then released and driven by the force of the first biasing component to in turn drive the piston toward the second position,
   and wherein the movement of the first actuating component is independent of the stroke of the piston.

In another aspect the present invention consists in a method of dispensing a fluid for animal welfare, comprising or including the steps of,
   A user driving a user operated handle which in turn drives a first actuating component,
   Tensioning a first biasing component via the first actuating component,
   Retaining a second actuating component against the tension,
   Providing a trigger event to release the second actuating component to in turn be driven by the tension,
   The second actuating component then driving a piston within a barrel which is adapted to then dispense a fluid when present from the barrel.

In another aspect the present invention consists in a kit of parts for a applicator including a handle body and a dose assembly as herein described with reference to any one or more of the accompanying drawings.

In another aspect the present invention consists in an applicator as described herein with reference to any one or more of the accompanying drawings.

Throughout the description and the claims, all reference to pressures are to gauge pressures, i.e. pressure relative to the ambient pressure. Therefore, a reference to zero pressure means ambient pressure. Reference to negative pressure means suction.

Reference to a partial vacuum is any pressure below ambient pressure but greater than a total vacuum.

Reference to the "upstream" direction is towards the direction in the fluid flow path from which fluid enters the applicator. Reference to the "downstream" direction is to the direction in which the fluid normally flows.

As used herein the term "and/or" means "and" or "or", or both.

As used herein "(s)" following a noun means the plural and/or singular forms of the noun.

The term "comprising" as used in this specification means "consisting at least in part of".

When interpreting statements in this specification which include that term, the features, prefaced by that term in each statement, all need to be present, but other features can also be present. Related terms such as "comprise" and "comprised" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

The entire disclosures of all applications, patents and publications, cited above and below, if any, are hereby incorporated by reference.

This invention may also be said broadly to consist in the parts, elements and features referred to or indicated in the specification of the application, individually or collectively, and any or all combinations of any two or more of said parts, elements and features, and where specific integers are mentioned herein which have known equivalents in the art to which this invention relates, such known equivalents are deemed to be incorporated herein as if individually set forth.

Other aspects of the invention may become apparent from the following description which is given by way of example only and with reference to the accompanying drawings.

BRIEF DESCRIPTION OF THE DRAWINGS

Preferred forms of the present invention will now be described with reference to the accompanying drawings in which.

DETAILED DESCRIPTION OF THE INVENTION

Figure 1:
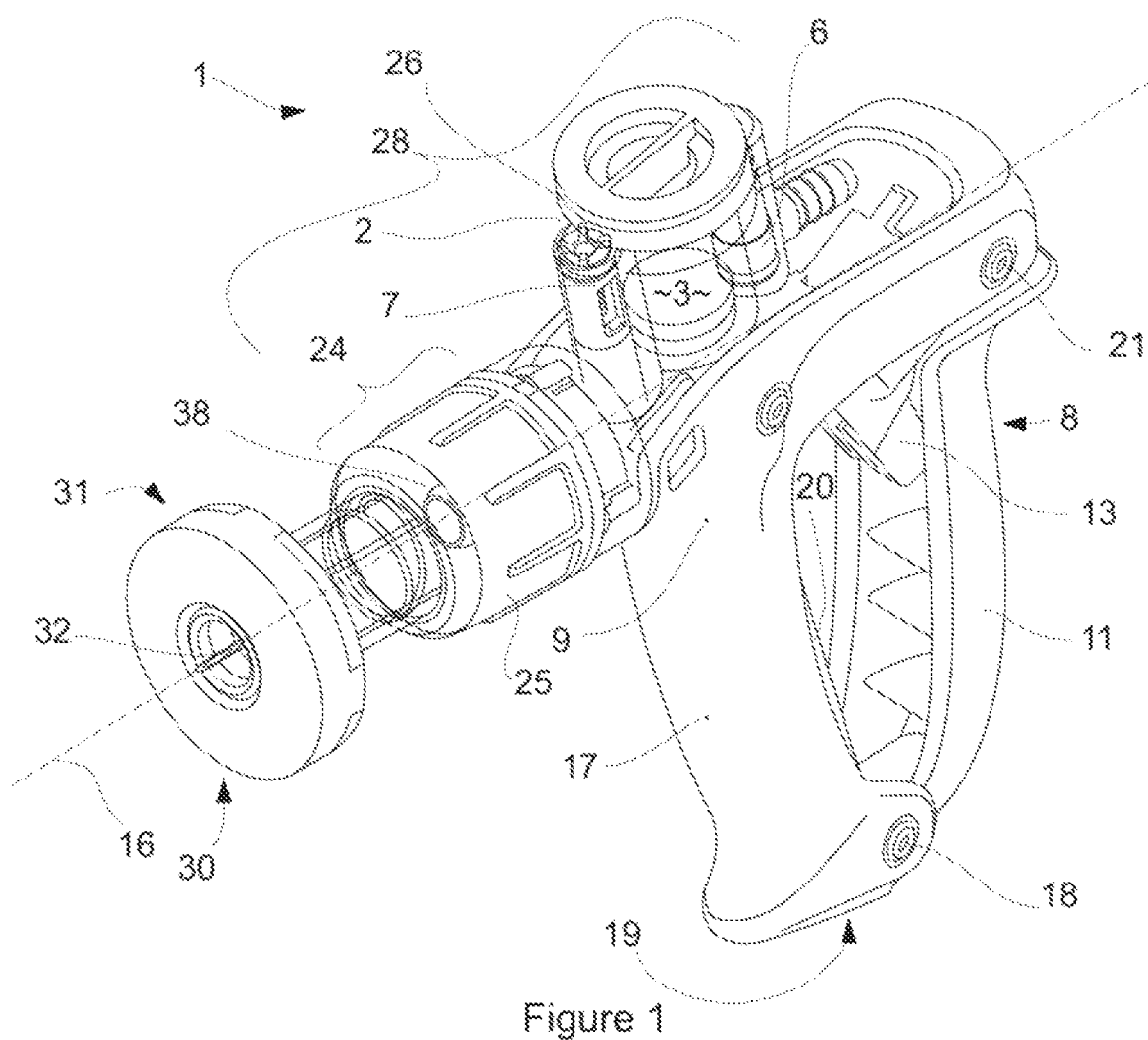
FIG. 1 Shows an isometric view of one form of the applicator showing the barrel and piston out of line with the main axis of the applicator, in this case the applicator is configured with a marking pad, needle and needle guard for marking and applying a subcutaneous injection, FIG. 2 Shows a side view of the embodiment of FIG. 1, FIG. 3 Shows a plan view of the embodiment of FIG. 1, FIG. 4 Shows a front view of the embodiment of FIG. 1, FIG. 5 Shows a rear view of the embodiment of FIG. 1, FIG. 6 Shows a bottom view of the embodiment of FIG. 1, FIG. 7 Shows an exploded isometric view of the body and associated components of the embodiment of FIG. 1, FIG. 8 Shows a further exploded view of the embodiment of FIG. 1, showing the marker pad and retaining ring, FIG. 9 Shows a further exploded view of the embodiment of FIG. 1, showing the second trigger component, needle guard, biasing spring and locking barrel, FIG. 10 Shows a cross section through a vertical plane along the main axis of the applicator of FIG. 1, FIG. 11 Shows a close up in isometric of the cross-section of FIG. 10 with the dosing body removed showing the handle body components, FIG. 12 Shows a further isometric view of FIG. 11, FIG. 13 Shows a further cross section in isometric with some of the active parts of the piston actuator shown, FIG. 14 Shows a further view of FIG. 13, with the second trigger component included, FIG. 15 Shows in side view FIG. 14, with the user operated handle actuated to move, in this case by rotation, the first actuating component to tension the first biasing means, FIG. 16 Shows a further view of FIG. 15 where the second trigger component is moved, in this case by sliding, to in turn release the first trigger component, FIG. 17 Shows a further view of FIG. 16, where release of the first trigger component allows the tension or spring force of the first biasing means to drive the second actuating component to in turn drive the piston, via a piston shaft, towards the second position to release the dose in the barrel, and FIG. 18 Shows a further view of FIG. 17 in isometric view.

Preferred embodiments will now be described with reference to FIGS. 1 through 18.

The general layout of the applicator 1 is shown in FIGS. 1 through 10. The applicator 1 consists of a body 9 from which is mounted, and mainly housed, the piston actuator assembly 8. Connected to the body 9 is the dose assembly 28. The dose assembly 28 is removable from the body 9 resulting in two main separable assemblies.

The applicator 1 has an applicator end 30 where the application is made to the animal. In the embodiment shown the applicator end has a marking pad 31 with an aperture there through for the application to be applied through. The application in this embodiment is via an injector 32 which is clearly visible, but is sheathed and protected by the marking pad 31 and the trigger portion 22.

However in other embodiments the marking pad 31 need not be present, when for example marking is not required.

Figure 17:
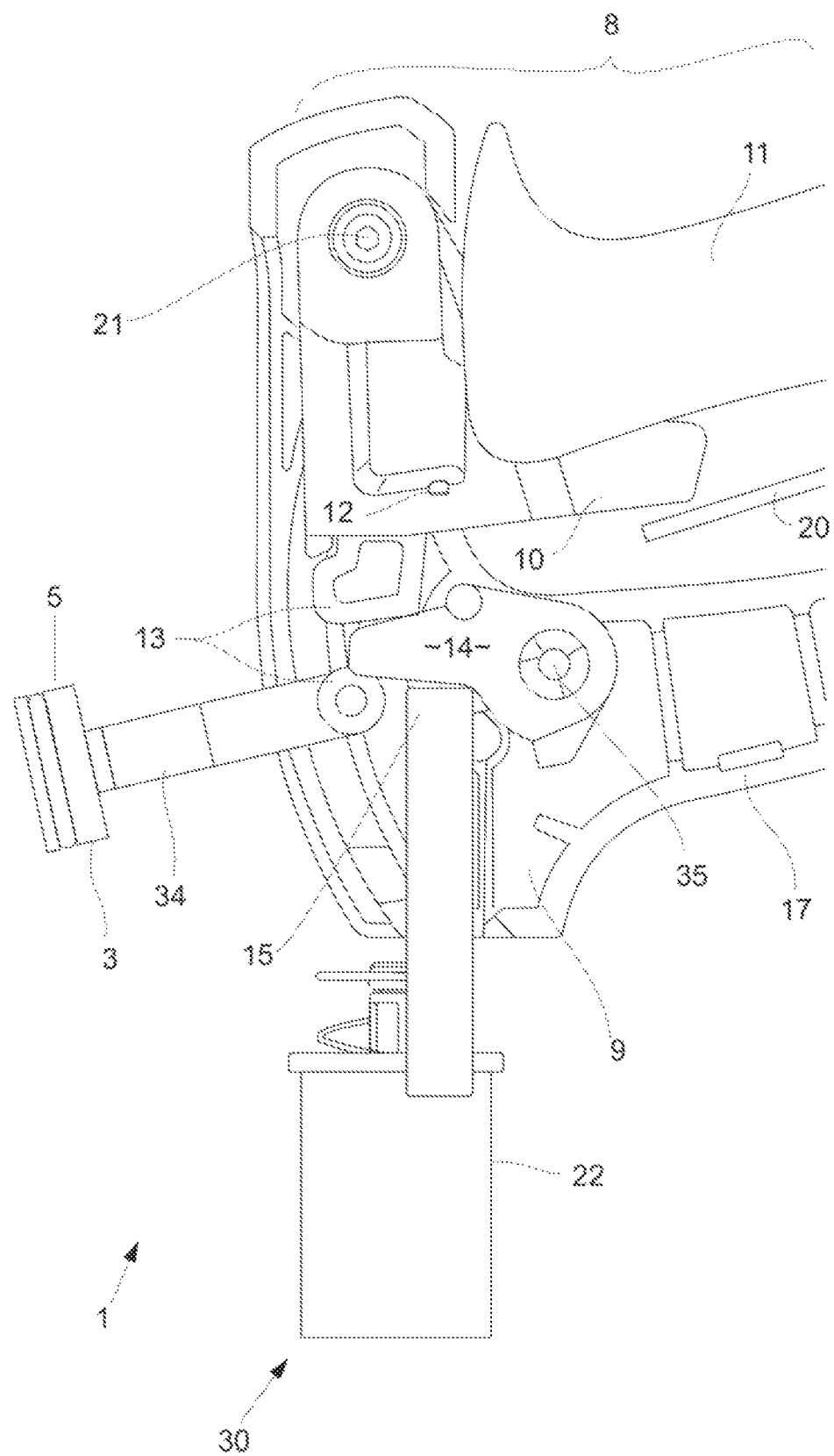

Shown also is an optional locking portion 24, which in the embodiment shown takes the form of a locking barrel 25. When fitted rotation of the locking barrel one way will enable a second trigger component 15 to slide (described below). Rotation in the other direction will disable the second trigger component 15 from moving. In the embodiment shown the locking portion rotates and blocks the sliding motion of the sheath which is transmitted to it by, in this case, contact of the marking pad 31 with the animal when applying a subcutaneous injection. Movement of the sheath, which is connected to the second trigger component, in one example as shown in FIG. 17, then moves the second trigger component (when enabled) to allow firing or deployment of the piston and hence dose delivery.

The sheath may have other attachments to it to contact a surface or other wise of the animal, to slide the sheath to enable the piston actuator assembly. When the attachment is removed from the surface, or otherwise, or the animal, the sheath is biased to extend by a spring, and so disable the piston actuator assembly. In other forms, not shown, the user may simply slide the sheath, or an attachment thereto, back to enable the piston actuator assembly. In other embodiments the sheath may not present, and attachments that move on contact with the animal surface, may be connected directly to the second trigger portion, or part thereof.

Such a lockout system provides safety to the user and animal and goes a long way to ensuring the applicator will only release the medication, when against a surface of an animal. This is particularly important when the medication is applied sub-cutaneously to prevent accidentally "stick" injuries for example to the user, regardless of whether medication is also released into the user.

As shown the applicator 1 has a pistol grip for the user consisting of a handle component 17 which extends from and is connected to the body 9. At a distal end 19 of the handle component 17 is a first pivot point 18 from which is pivoted the user operated handle 11. It is this the user operates by squeezing to bring the two handle components 11 and 17 together to initiate the piston actuator assembly.

Figure 2:
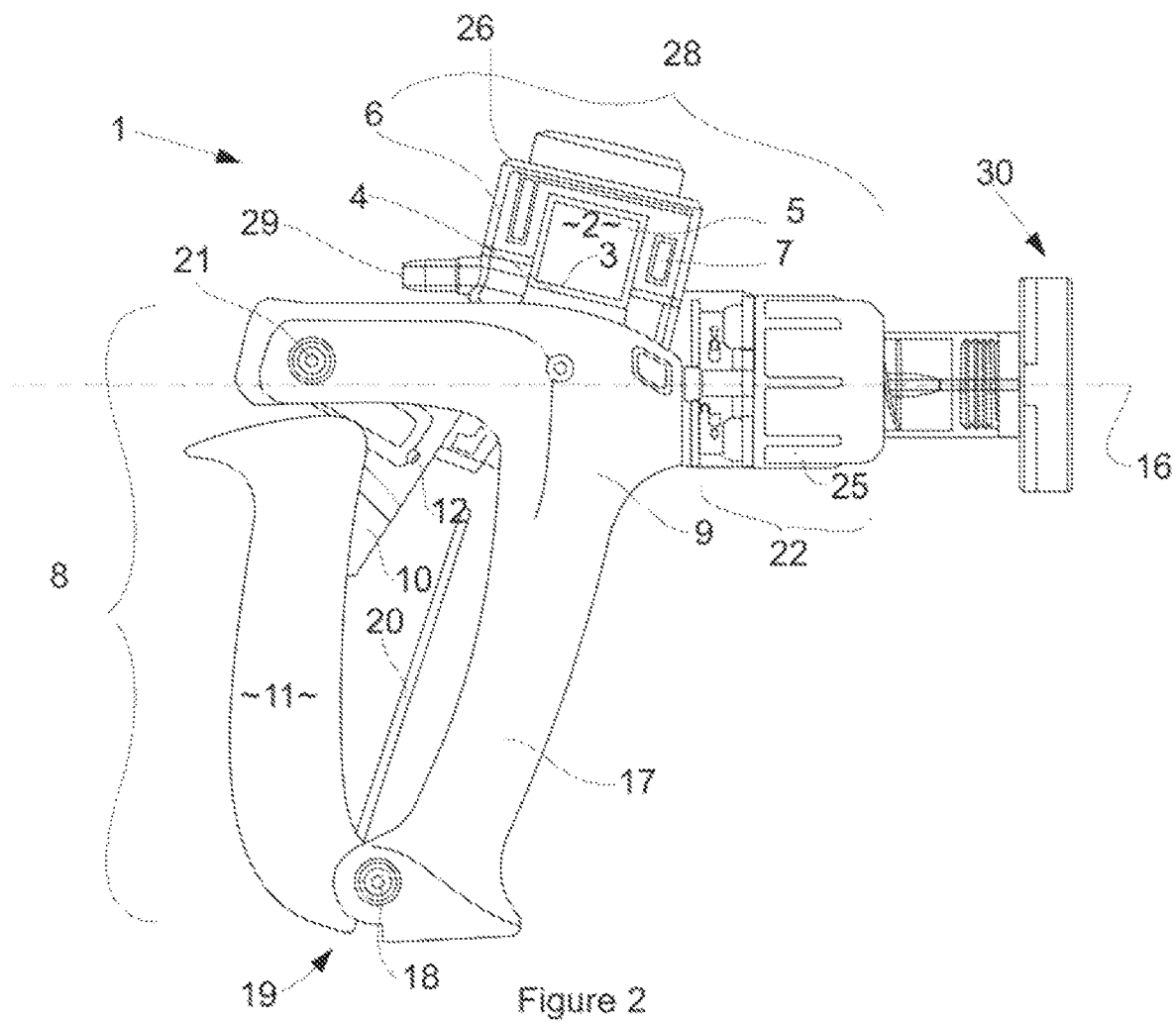
Figure 3:
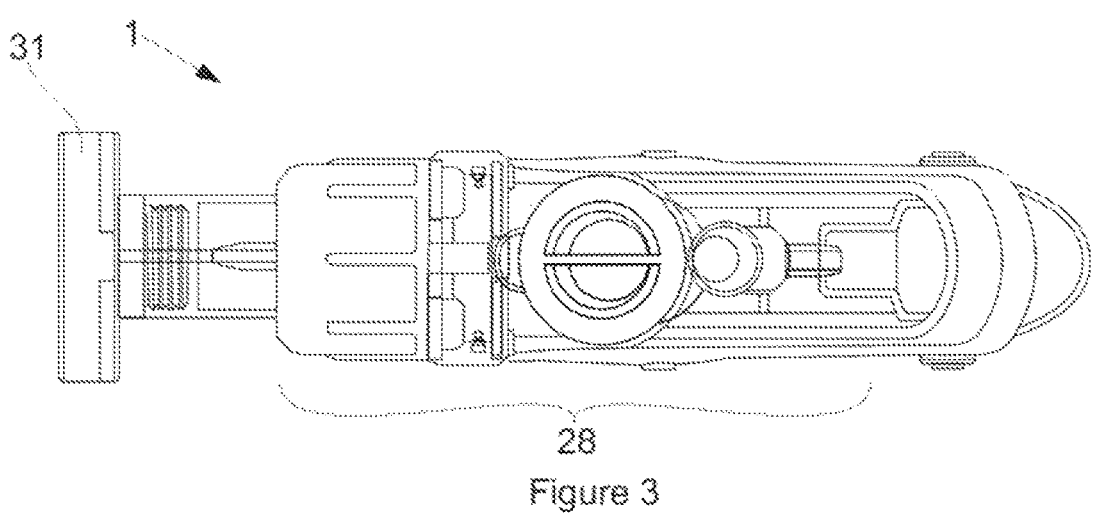
Figure 4:
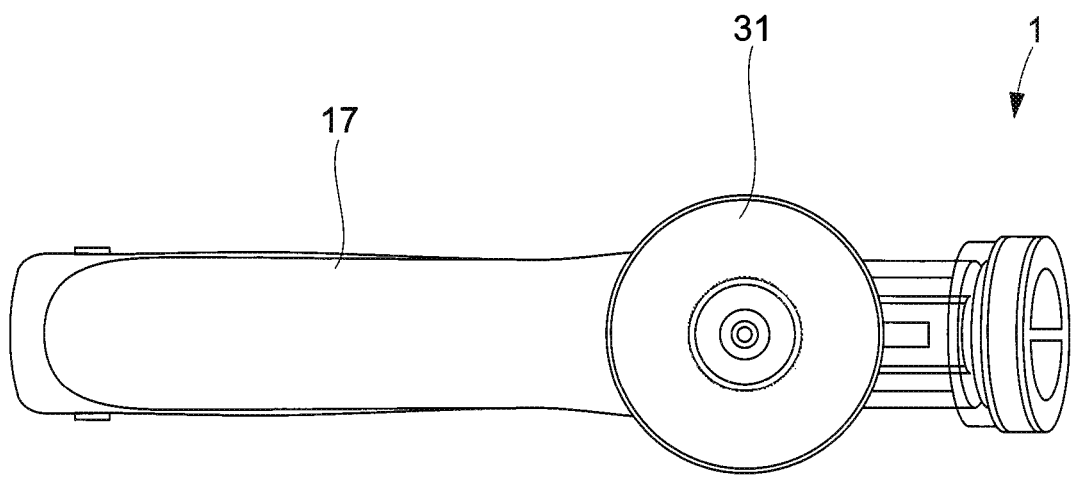
Figure 5:
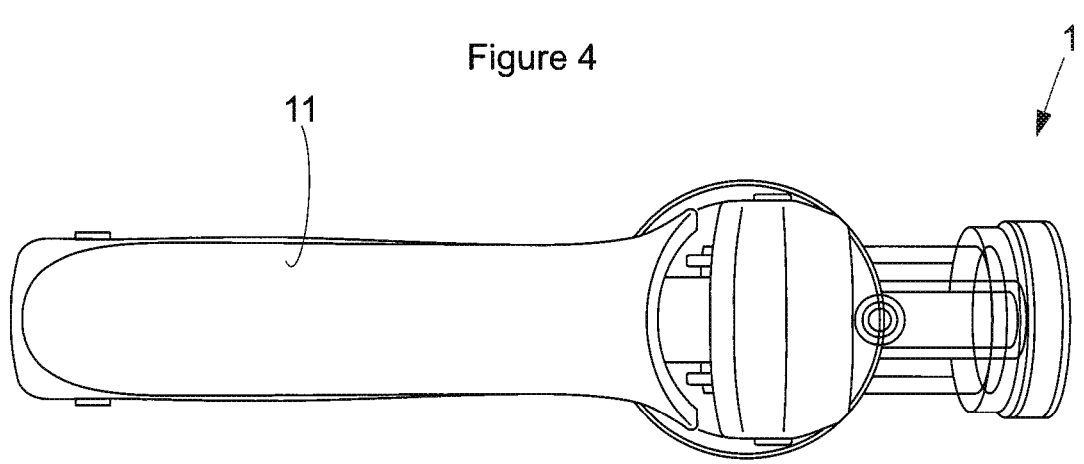
Figure 6:
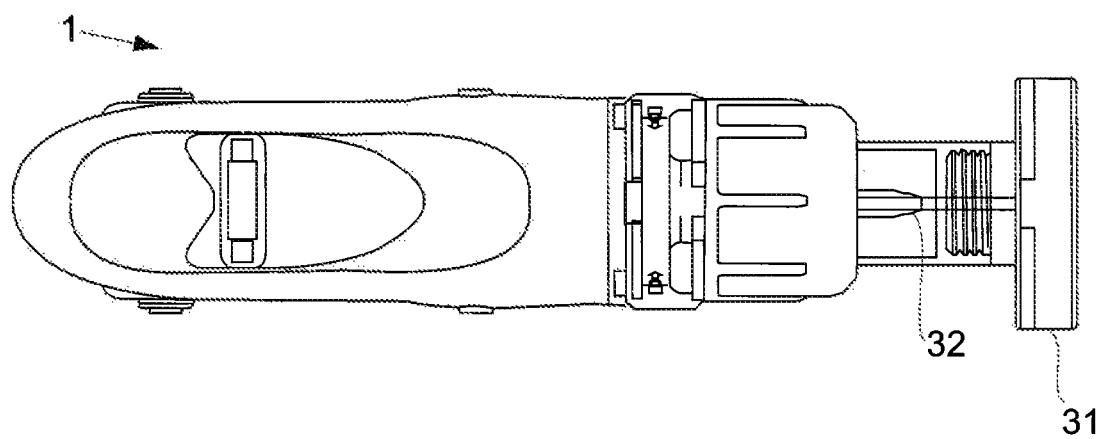
Figure 7:
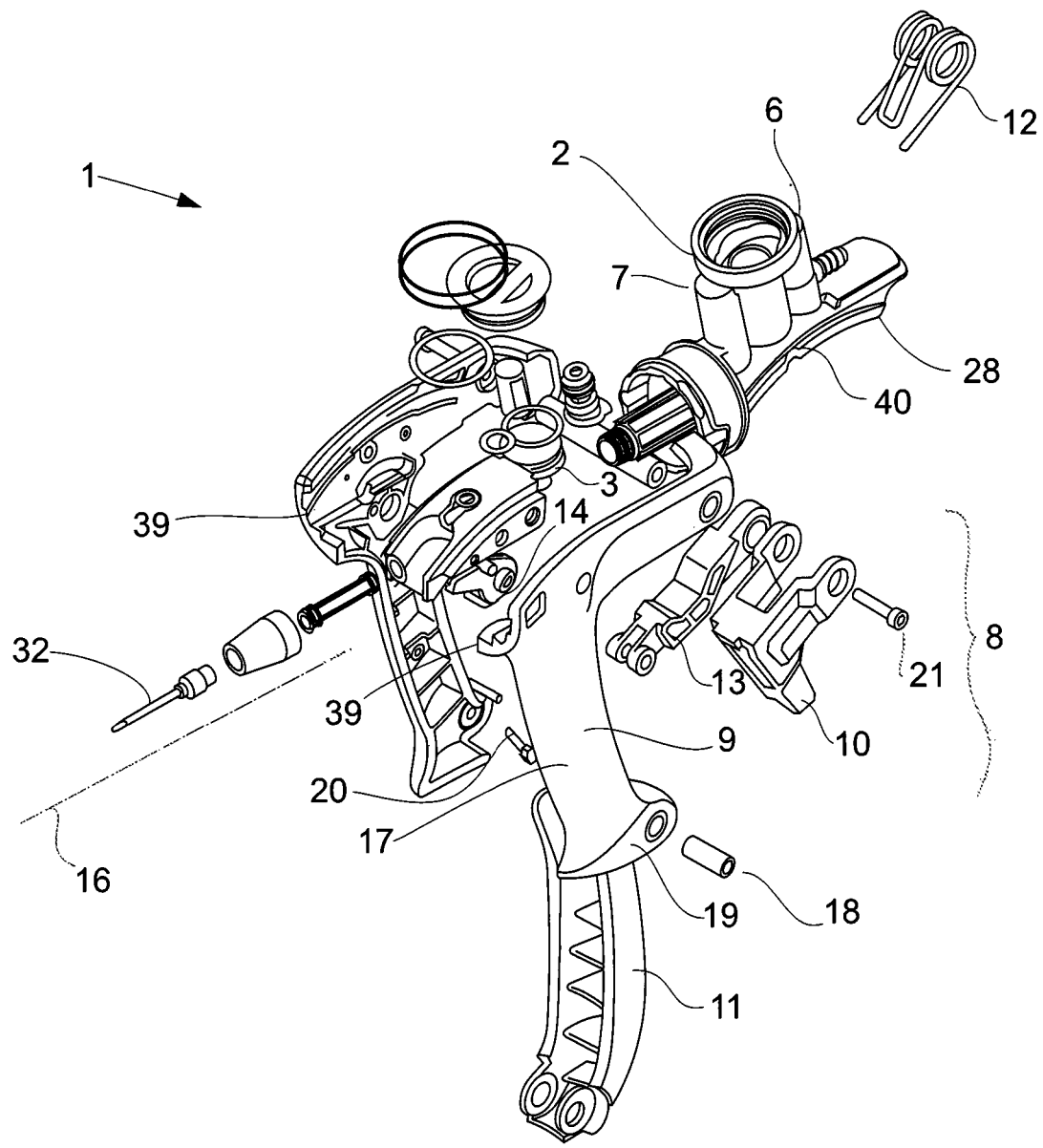
Figure 8:
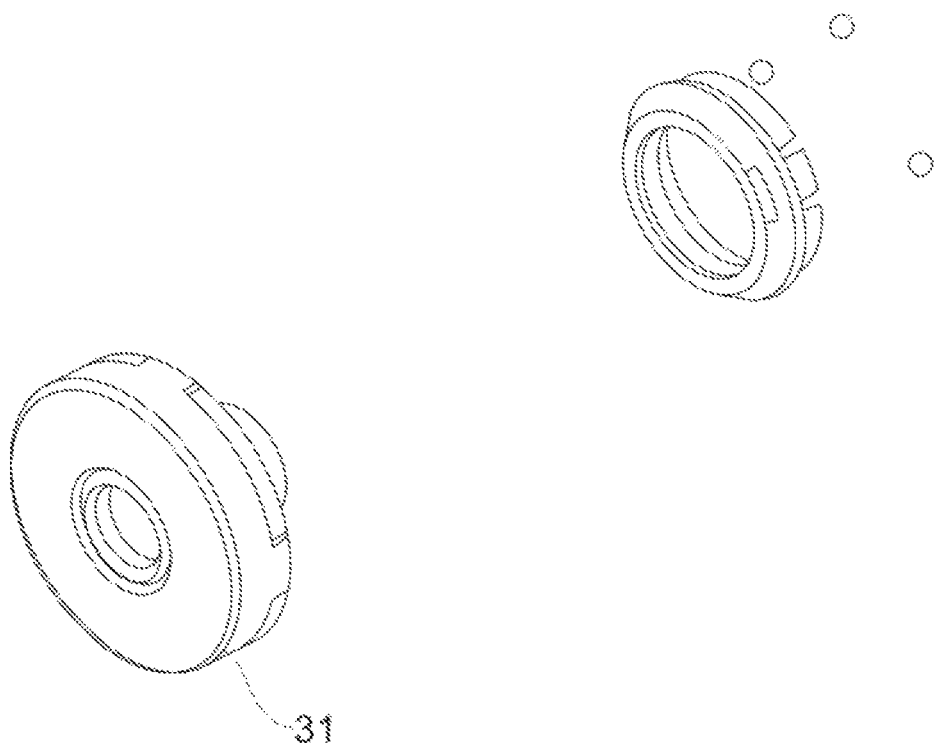
Figure 9:
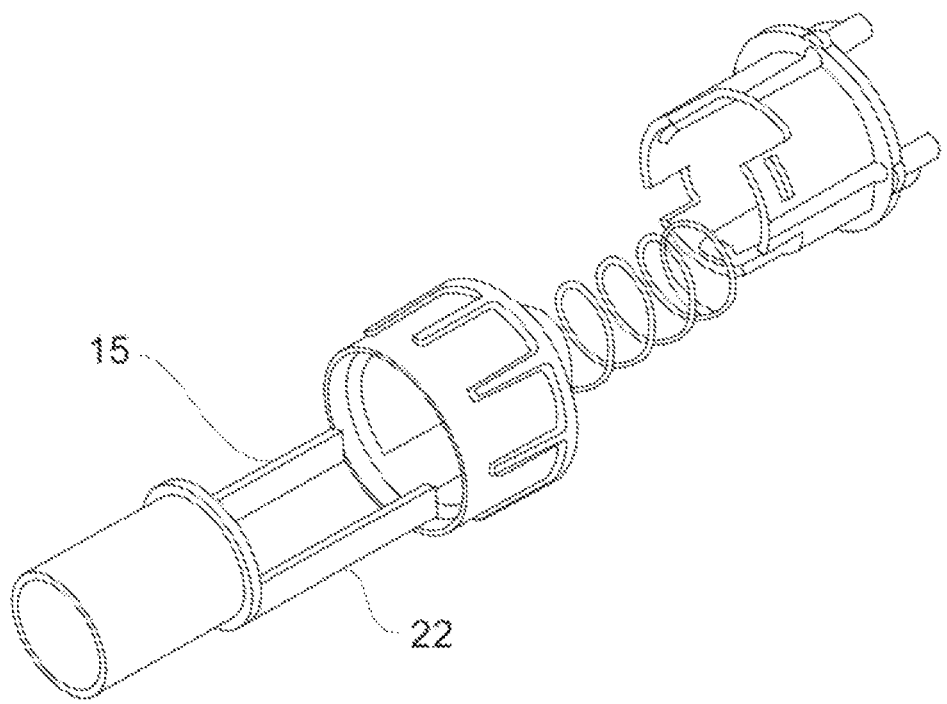
Figure 10:
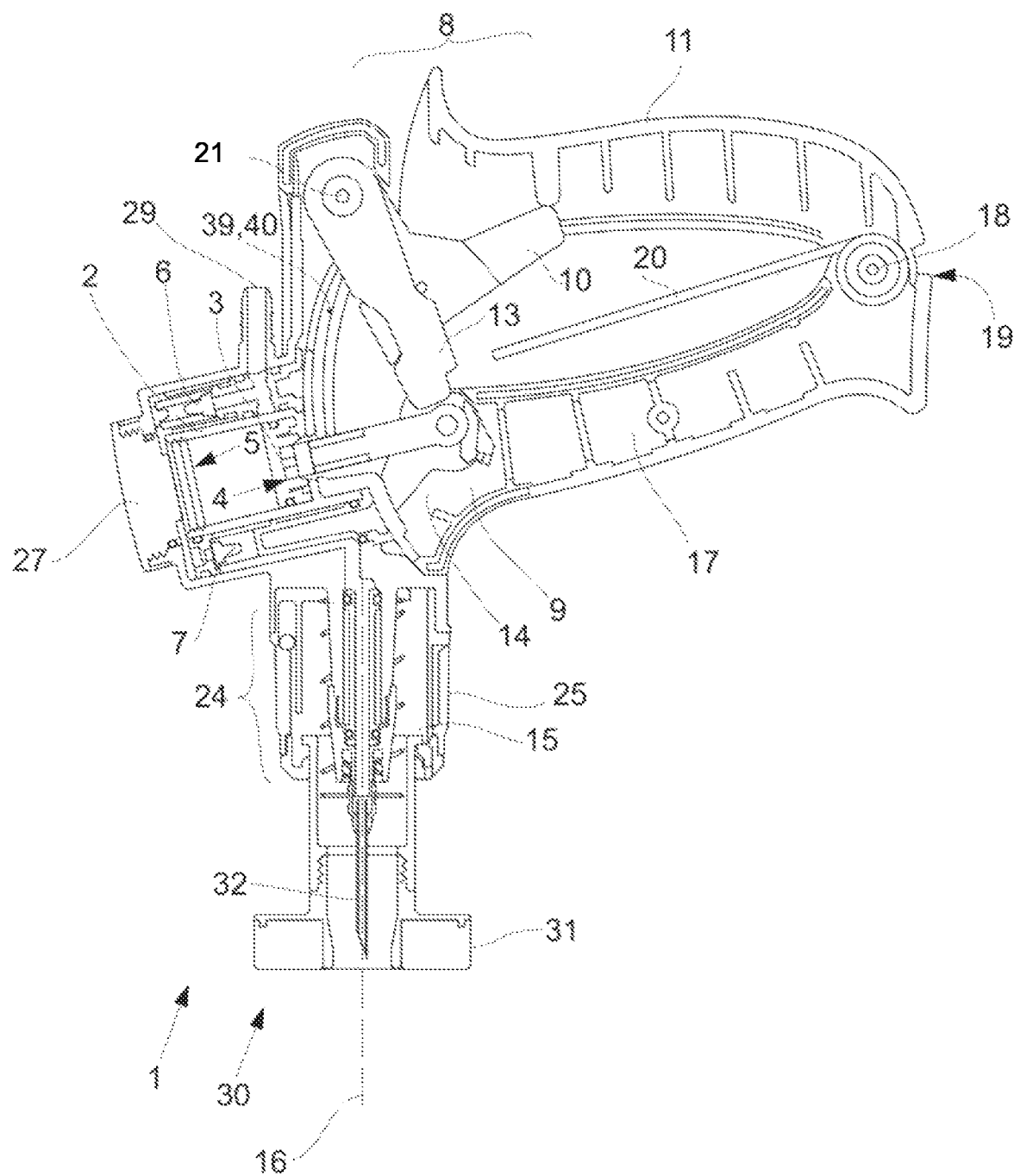
Figure 11:
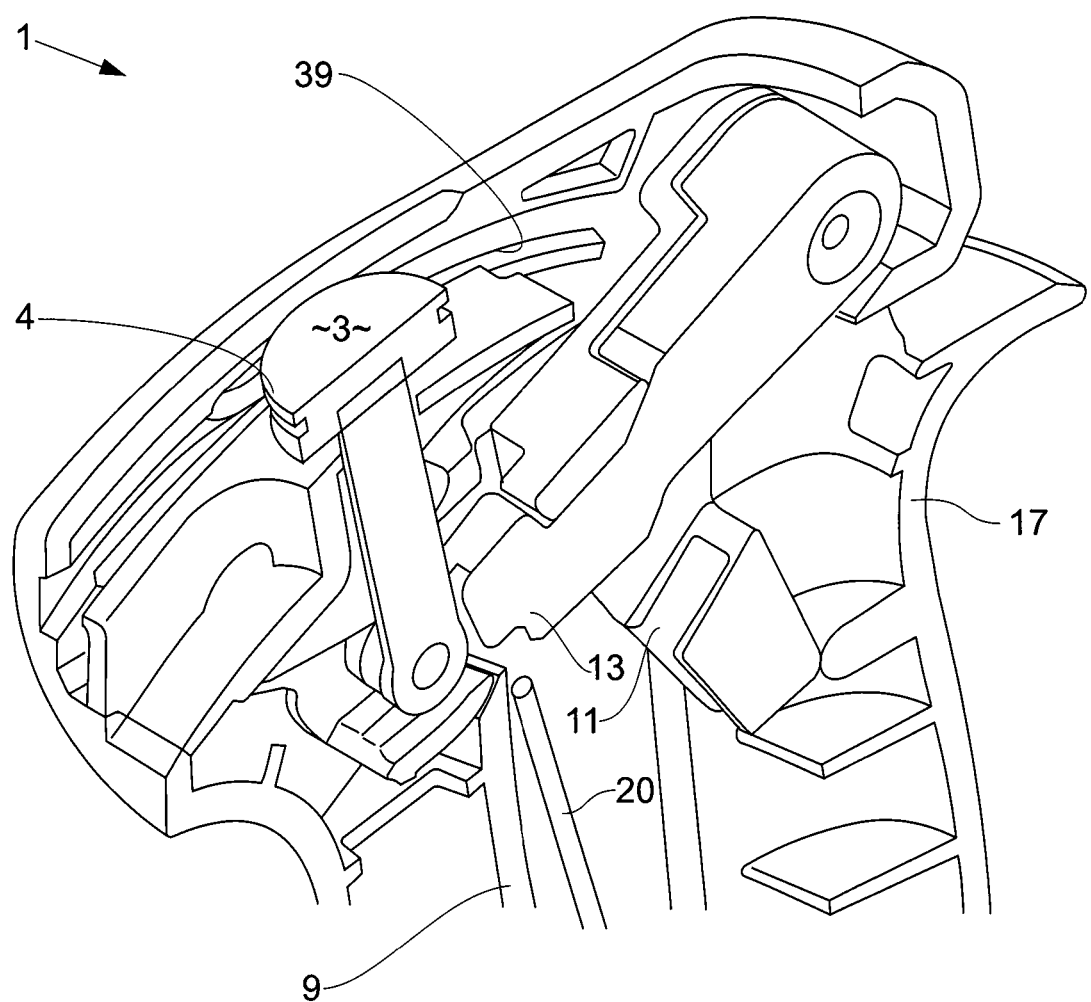
Figure 12:
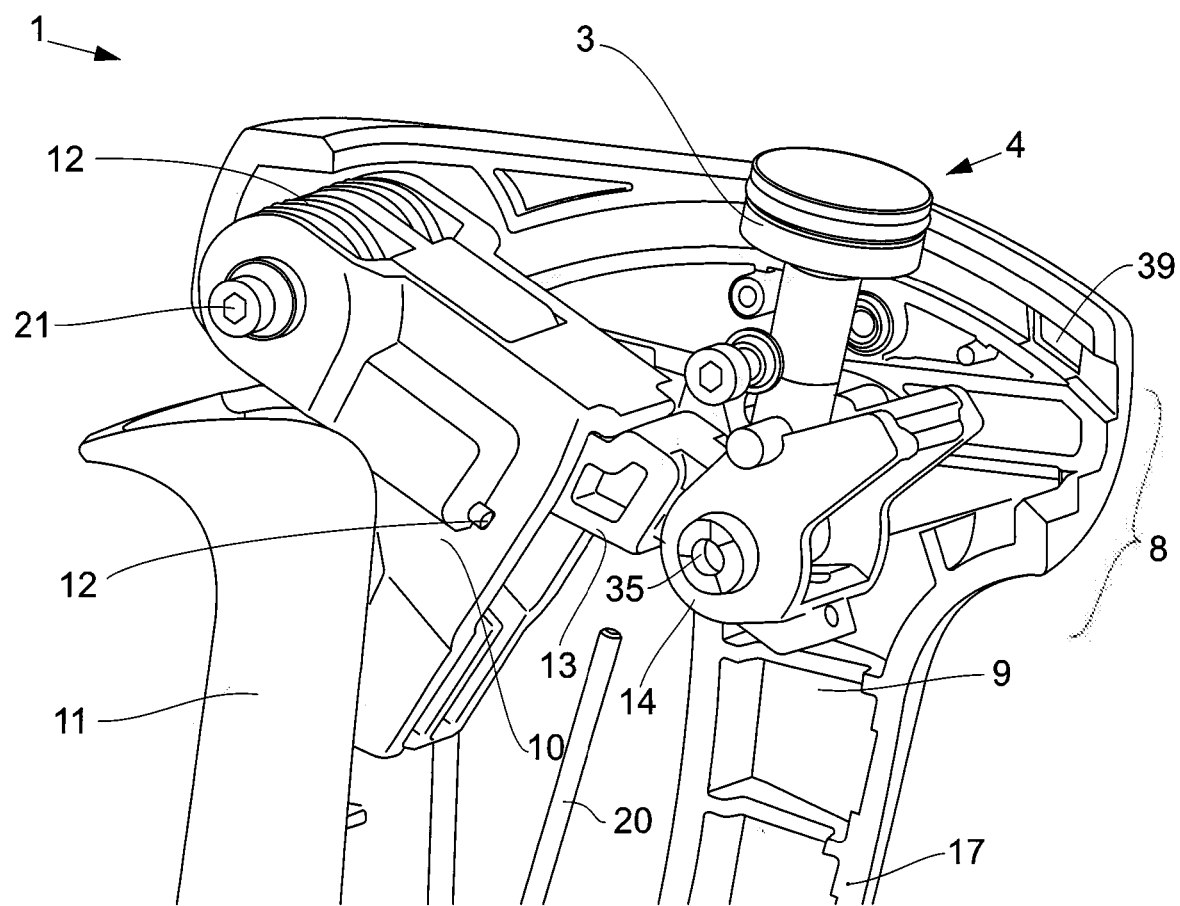

The dose assembly 28, shown for example in FIGS. 2, 7 and 10, consists of a fluid inlet 29 that connects to a supply of fluid, for example by flexible connection to a back pack, or to a directly mounted vial or similar. The fluid inlet 29 leads to a one way inlet valve 6 which in turn leads to the barrel 2. Inside the barrel is a piston 3 that is slidingly sealed and can stroke from a first position 4 as shown to a second position 5, when allowed, to expel fluid in the barrel 2. The fluid is expelled as the piston 3 strokes to the second position 5 and exits the barrel 3 to the outlet valve 7 which then leads to fluid outlet 38 at or toward the applicator end 30. The fluid outlet can have a number of differing effectors connected to it, in this case it has an injector 32, connecting in a known way using a hollow nut to hold it in place. The device end effector which applies the fluid to the animal could, instead of the injector 32, be configured in known ways to deliver the fluid, topically, nasally, orally or otherwise to the animal.

While shown here as an injector 32 for example a needle, it may also take the form of a topical surface application component, a nasal application component, oral application component or other application component as needed. Thus, the application component able to be removed and another replaced as needed to suit the particular use of the applicator 1 as needed.

The configuration of the applicator 1 as shown in FIG. 1 is ideally suited for subcutaneous injection of animals. When other application components, or effectors are attached in place of the injector 32, then the applicator 1 may be used as described to apply medication nasally, orally, topically, or to any other orifice or surface of the animal for example but not limited to swine, bovine, equine, ovine or other non-human animal.

The present invention has a unique orientation of the barrel. As shown the barrel 2, piston 3 and valves 6 and 7 are oriented so they do not lie along the main axis 16 of the injector. Typically doing so has led to many inefficiencies in design, and also makes the applicator longer. By effectively folding the fluid path and barrel, piston and valves out of this axis it allows for a more compact and maneuverable applicator 1.

The dose assembly 28 as described above from fluid inlet 29 to fluid outlet 38 is also a unitary component and holds the piston 3, valves 6 and 7 and the barrel 2, and any components used to vary the stop of the piston at the second position 5, such as inserts 26, or a variable stop 27. The dose assembly 28, in one embodiment, can engage channels 39 in the body as shown with complimentary rails 40 (curved in the embodiment shown), or vice versa. In this way the dose assembly 28 and piston actuator assembly 8 as a handle assembly can be separated and joined. This allows quick change and servicing, but also where the barrel 2 is a fixed dose, allows changing of doses by changing the dose assembly 28 from a barrel 2 with one dose, to another dose assembly 28 with a barrel 2 of a differing dose.

The method of application and the piston actuator assembly will now be described with reference to FIGS. 7 through 18. The piston actuator assembly 8 consists of the user operated handle 11, which in turn bares on the first actuating component 10. The first actuating component 10 is pivoted from the second pivot point 21, which is mounted on the housing 42. Between the first actuating component 10 and a second actuating component 13 there is a first biasing component 12 (illustrated as a spring), as shown in FIG. 7. For convenience of assembly, manufacture and service and component reduction the first actuating component 10 (illustrated as a linkage), second actuating component 13 (illustrated as a piston actuator) and first biasing component 12 (or spring) all move around a second pivot point 21, however these need not be the case.

Figure 16:
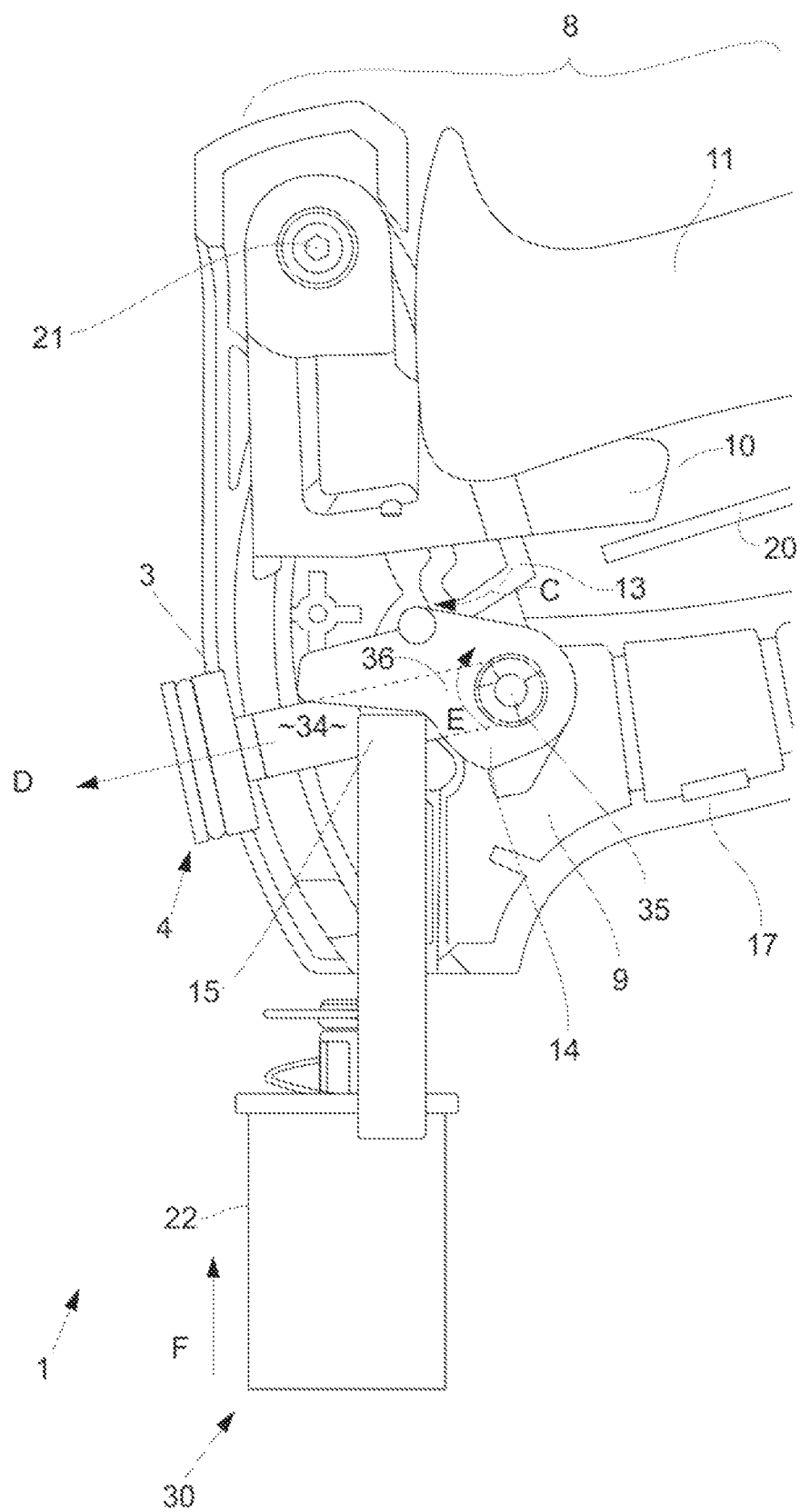

Rotation of the first actuating component 10 in the direction of arrow B (see FIG. 15), by movement of the user operated handle 11 when moving in the direction of arrow A (see FIG. 15), loads up the first biasing component 12 to apply a rotational force to the second actuating component 13 in the direction of arrow C (see FIG. 16). The second actuating component drives the piston shaft 34 and then the piston 3.

Figure 13:
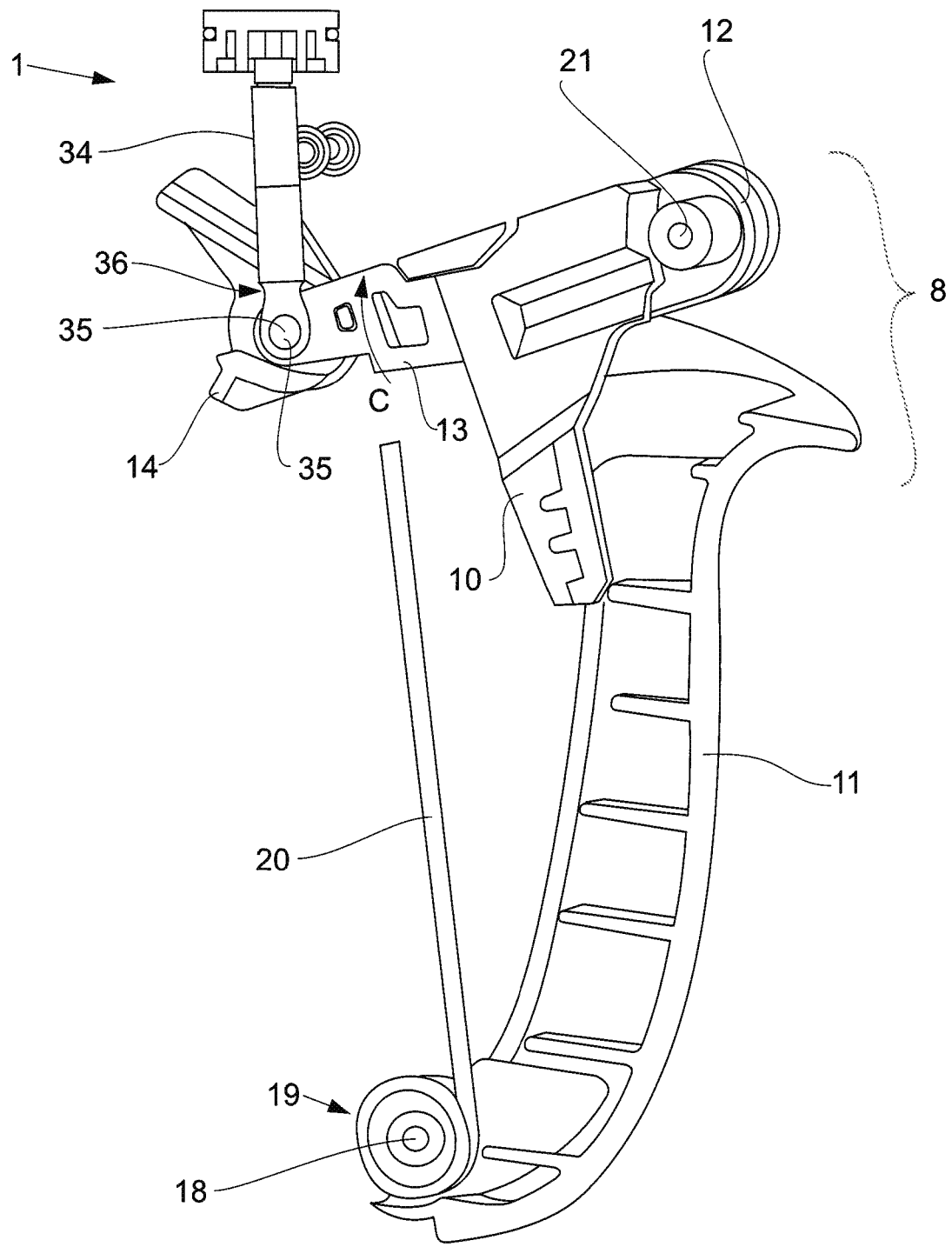
Figure 14:
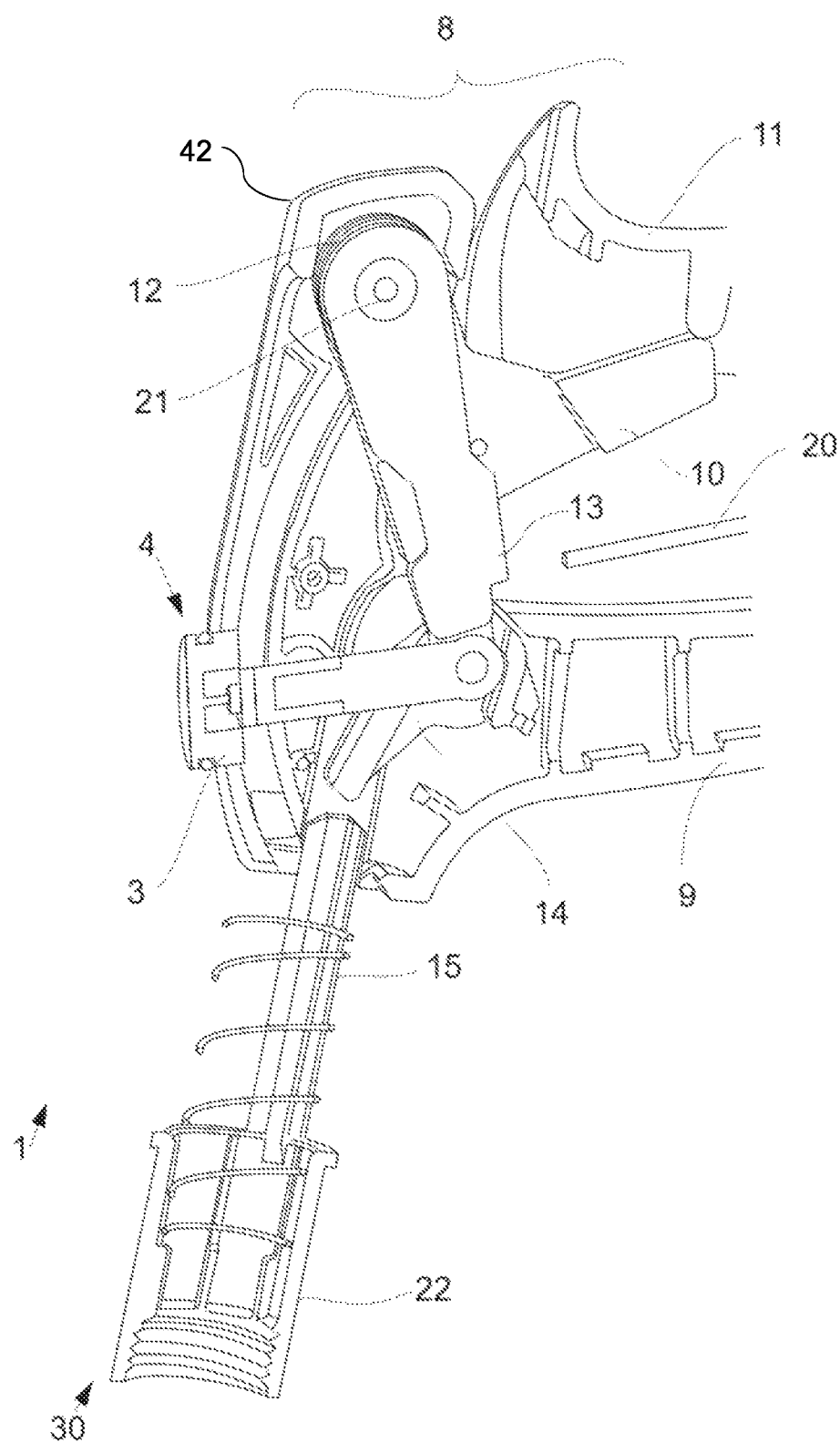
Figure 15:
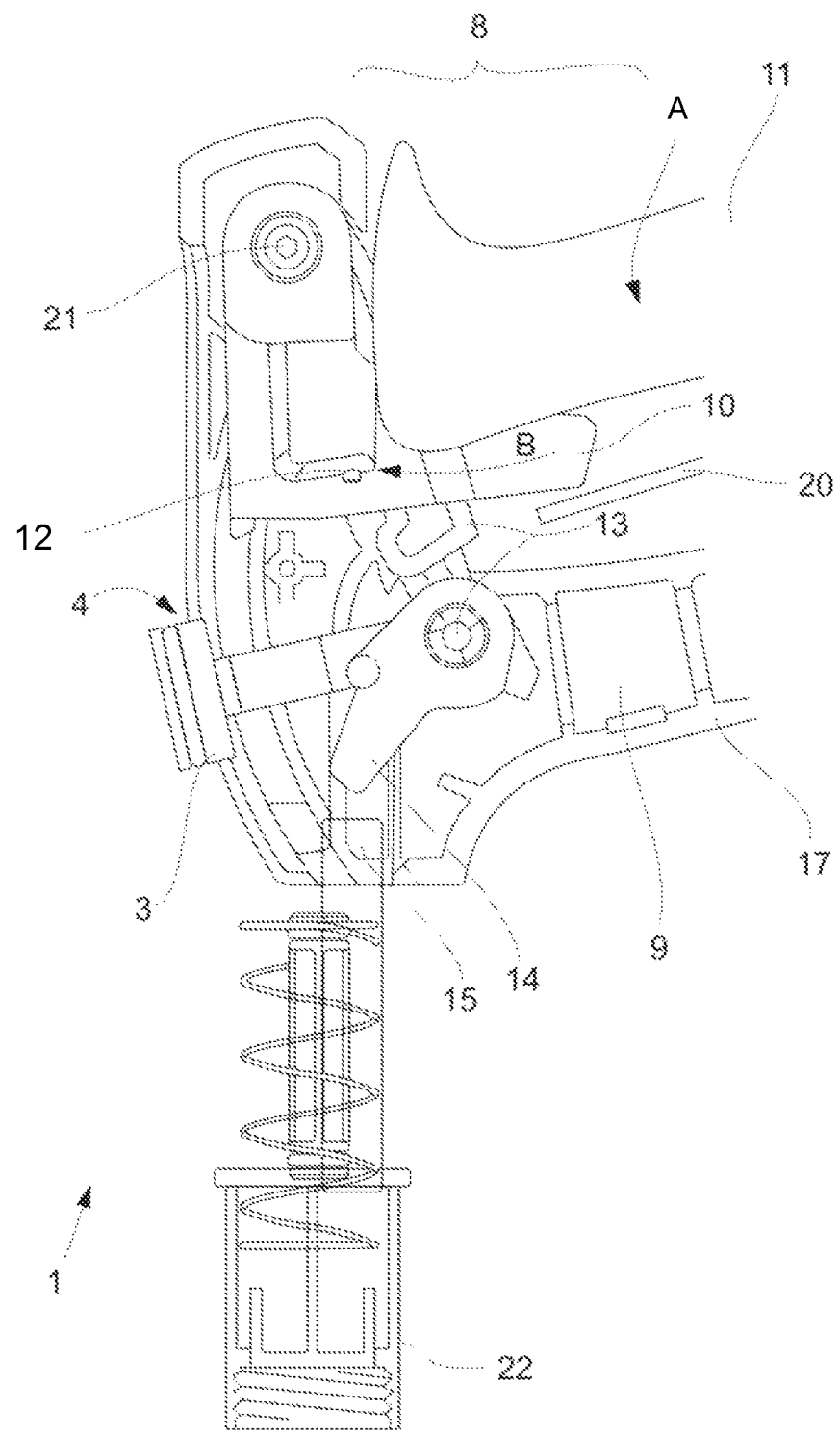

However, the second actuating component 13 is prevented from rotating in the direction C by the first trigger component 14. In the embodiment shown the first trigger component 14 has a piston shaft guide 36, that in FIG. 13 is out of alignment with the desired movement of the piston pivot. Thus the second actuating component cannot unload the spring force of the first biasing component 12.

The first trigger component 14 can rotate, when allowed, about the third pivot point 35 in the direction of arrow E as shown in FIG. 16. The first trigger component 14 may be allowed to rotate in several ways. This first of these is by activation of a second trigger component 15. The second trigger component will cause the first trigger component to rotate in the direction E, until the piston shaft guide 36 is aligned with the direction of motion indicated by arrow D (see FIG. 16) of the piston shaft 34.

Movement of the second trigger component 15 in the embodiment shown in caused by location of the marker pad 31 against the skin of the animal. This causes the sheath and trigger portion 22, and hence second trigger component 15 to slide in direction F as shown in FIG. 16.

In this way the applicator 1 is located against an animal, the marker pad 31 contacts the skin, the injector 32 pierces the skin as the sheath, trigger portion 22 and second trigger portion 15 slide in direction F, to this cause or allow rotation of first trigger portion 14. After initial rotation in Direction E, the force loaded against the second actuating component takes over and causes the remaining rotation of first trigger component 14.

In other embodiments the first trigger portion may simply be biased against rotation in direction E until there is sufficient force generated by the first biasing component 12. In this configuration the second trigger component may not be present, or at least may not operate as part of releasing and deploying the piston. The applicator in this configuration may again be used to deploy medication to the surface, subcutaneous, orifice or other surface of the animal with the correct effector in place for delivery to that surface.

Figure 18:
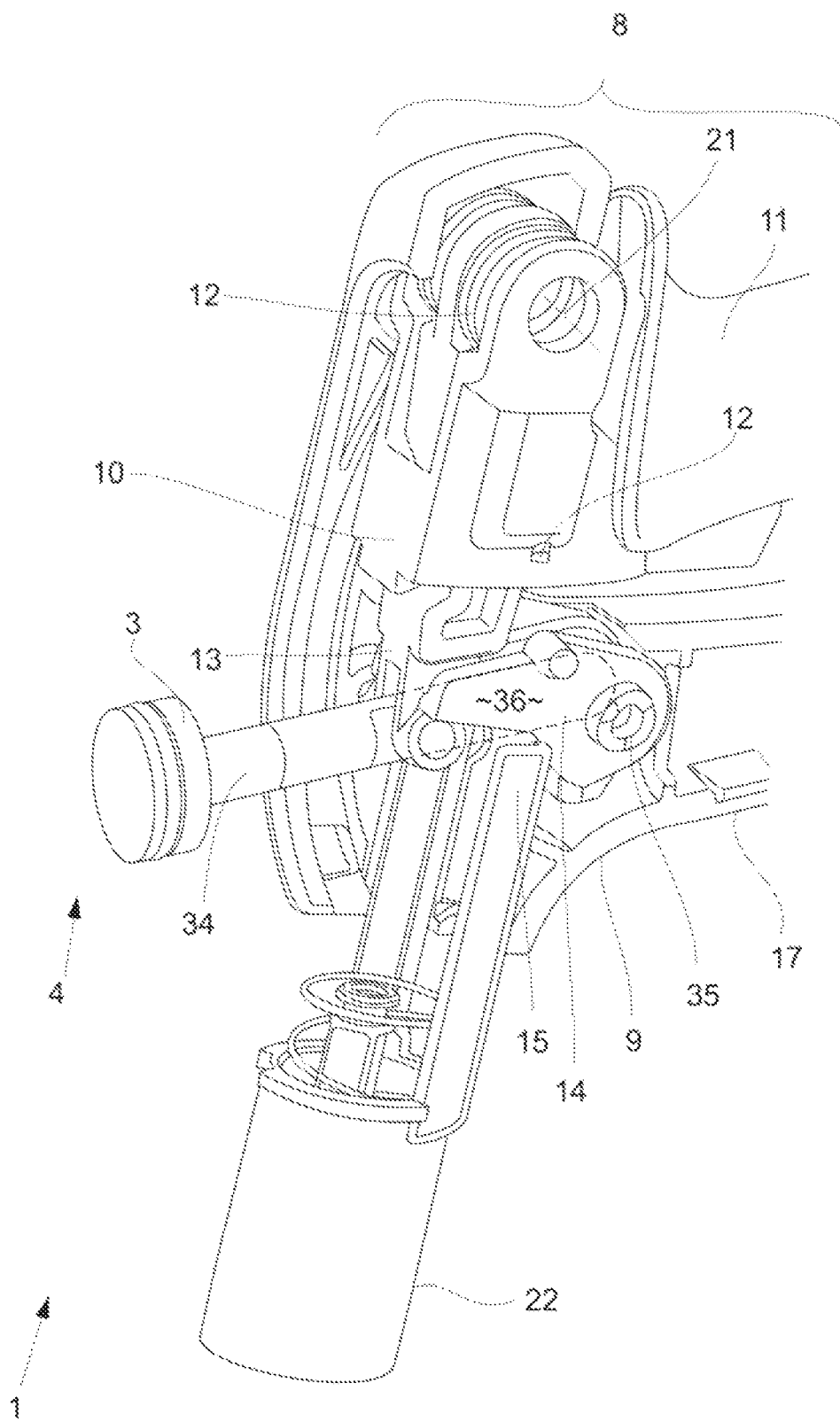

Once the piston shaft guide 36 is aligned with the Direction D, the second actuating component, under action of the first biasing component 12 drives the piston shaft in Direction D, and hence also piston 3 from the first position 4 (shown in FIG. 16) to the second position 5 (shown in FIGS. 17 and 18). Thus, the fluid in the barrel is dispensed from the fluid outlet and into (in this case) or onto the animal.

The process is similar when the application is to the surface, or orifice of the animal. The allows second trigger portion, when present, is moved by contact with the animal surface or orifice, to then allow deployment of the piston, the handle having been contracted by the user.

Once the dose has been delivered the process is reversed. The user releases the user operable handle 11 to move in the opposite to Direction A under action of second biasing component 20. This in allows the first and second actuating components to move in the opposite to Direction B. First and second actuating components are also acted on by first biasing component 20 at the same time. In turn this pulls the piston shaft 34, which is pivotally connected to second actuating component 13, and piston 3 down which in turn draws another dose of fluid into the barrel 2. Release of the marker pad 31 allows the sheath 3-to recover the injector 32 and the trigger portion 22 and second trigger component 15 to all slide in the opposite direction to F. This allows first trigger component to return to its locking position and the applicator is now set to deliver another dose.

The result is a more compact applicator 1 that also has the movement of the user operated handle 11 and handle component 17 having the ideal range of motion regardless of the dose that is delivered—from a small dose to a large dose the range of motion of the handles 11 and 17 is unchanged. The movement of the piston 3 is disconnected so that the distance of movement of the piston does not affect the distance of movement of the handle 17 from a range of motion perspective, and a force the user needs to apply to the handle 17.

The applicator can therefore be used and configured and used in a number of ways, in addition to the effector for the particular dosing topically, orally, nasally, subcutaneously, or other surface of the animal.

The most full featured is when the lockout feature using the locking barrel 25 and second trigger component 15 is present. In this form the user can squeeze the handle 11 to charge the trigger mechanism, and when the locking barrel is in the unlocked position, the second trigger component 15 is free to move, and thus when a surface, or otherwise of the animal is contacted the tension in the first biasing component 12 is released and the piston moved to the second position and the medication delivered or applied.

Alternatively the applicator, once the locking barrel 25 is in the enable position, to allow movement of the second trigger component, the applicator 1 is located against the animal surface or orifice so the second trigger component is enabled (that is slid the necessary distance inwardly along the main axis 16) to unlock the first trigger component 14. Then, when the user squeezes the handle 11, the piston will be driven to the second position to deliver the dose.

The same is achieved if the lockout feature and locking barrel 25 are not supplied, again with pre-loading of the first biasing component 12, and firing or release by movement of the second trigger component 15 to drive to piston to deliver the dose. Alternatively with the second trigger component slid into the release position (as described above), the user can then squeeze the handle 11 to then drive the piston to deliver the dose.

The handle may also be supplied on its own as a spare part, to then be associated with a barrel and dose assembly.

The foregoing description of the invention includes preferred forms thereof. Modifications may be made thereto without departing from the scope of the invention.

The invention claimed is:
1. An applicator comprising or including,
at least one barrel;
a piston moveable within the at least one barrel to stroke between a variable first position and a second position, wherein, in use, movement of the piston towards the variable first position can draw a first fluid into the at least one barrel, and movement of the piston towards the second position can force the first fluid out of the at least one barrel;
at least one fluid inlet valve to allow the first fluid to flow into the at least one barrel at least under action of the piston, and at least one fluid outlet valve to allow the first fluid to flow out of the at least one barrel at least under action of the piston;

a piston actuator assembly, housed at least in part within a body, operable to move the piston towards the second position to dispense the first fluid from the applicator, wherein the piston actuator assembly comprises a linkage driven by a user operated handle to pivot and tension a first spring, a piston actuator held in position against a force of the first spring, a first trigger component that holds the piston actuator in place until a required force is reached by the first spring, or a second trigger component releases the first trigger component, whereby the piston actuator is then released and driven by the force of the first spring to in turn drive the piston toward the second position;

and wherein a movement of the linkage is independent of a stroke of the piston;

wherein the linkage and the piston actuator are pivotally mounted on a housing from a common second pivot point, wherein the linkage links the piston actuator in rotation when the user operated handle is released to unload the first spring.

2. The applicator according to claim 1, wherein the piston and the at least one barrel are not in line with the linkage and the piston actuator, but rather are at an angle to them, or a main axis of the applicator.

3. The applicator according to claim 1, wherein a handle component extends from the body and the user operated handle pivots from a first pivot point at a distal end of the handle component.

4. The applicator according to claim 3, wherein the user operated handle is driven to extend away from the handle component by a second biasing component.

5. The applicator according to claim 1, wherein the second trigger component is slidably moveable in line with a main axis of the applicator, and has a trigger portion that releases the first trigger component.

6. The applicator according to claim 1, wherein the second trigger component is biased away from the first trigger component.

7. The applicator according to claim 1, wherein the first trigger component is pivotally mounted from the housing.

8. The applicator according to claim 1, wherein there is a locking portion that locks to prevent movement of the piston actuator assembly, wherein the locking portion prevents or allows movement of the second trigger component, wherein the locking portion extends about the second trigger component.

9. The applicator according to claim 1, wherein the at least one barrel is replaceable to vary a dose of the applicator.

10. The applicator according to claim 1, wherein the at least one barrel can receive an insert to provide a stop of the second position of the piston to vary a dose of the applicator.

11. The applicator according to claim 1, wherein the at least one barrel has a variable stop to vary the second position of the piston to vary a dose of the applicator.

12. The applicator according to claim 1, wherein the at least one fluid inlet valve, at least one fluid outlet valve, piston and the at least one barrel can be removed as a dose assembly from the body.

13. An applicator to dispense a fluid or the like, comprising or including, at least one barrel;

a piston moveable within the at least one barrel to stroke between a variable first position and a second position, wherein, in use, movement of the piston towards the variable first position can draw a first fluid into the at least one barrel, and movement of the piston towards the second position can force the first fluid out of the at least one barrel;

at least one fluid inlet valve to allow the first fluid to flow into the at least one barrel at least under action of the piston, and at least one fluid outlet valve to allow the first fluid to flow out of the at least one barrel at least under action of the piston;

a piston actuator assembly, housed at least in part within a body, operable to move the piston towards the second position to dispense the first fluid from the applicator, wherein the piston actuator assembly comprises a linkage driven by a user operated handle to pivot and tension a first spring, wherein the first spring in turn provides a force against a piston actuator until the piston actuator is released to in turn drive the piston towards the second position and then dispense the first fluid, and wherein a movement of the linkage is independent of a stroke of the piston, wherein the linkage and piston actuator are pivotally mounted on a housing from a common second pivot point, wherein the linkage links the piston actuator in rotation when the user operated handle is released to unload the first spring.

14. The applicator according to claim 13, wherein the piston actuator is held in position against the force of the first spring, a first trigger component that holds the piston actuator in place until a required force is reached by the first spring, or a second trigger component releases the first trigger component, whereby the piston actuator is then released and driven by the force of the first spring to in turn drive the piston toward the second position.

15. A handle for an applicator, the handle adapted to move at least one piston in at least one barrel, to stroke between a variable first position and a second position, wherein, in use, movement of the at least one piston towards the variable first position can draw a first fluid into the at least one barrel, and movement of the at least one piston towards the second position can force the first fluid out of the at least one barrel; the at least one barrel having at least one fluid inlet valve to allow the first fluid to flow into the at least one barrel at least under action of the at least one piston, and at least one fluid outlet valve to allow the first fluid to flow out of the at least one barrel at least under action of the at least one piston;

the handle comprising, a piston actuator assembly, housed at least in part within a body, operable to move the at least one piston towards the second position to dispense the first fluid from the applicator, wherein the piston actuator assembly comprises a linkage driven by a user operated handle to pivot and tension a first spring, a piston actuator held in position against a force of the first spring, a first trigger component that holds the piston actuator in place until a required force is reached by the first spring, or a second trigger component releases the first trigger component, whereby the piston actuator is then released and driven by the force of the first spring to in turn drive the at least one piston toward the second position, and wherein a movement of the linkage is independent of a stroke of the at least one piston, wherein the linkage and piston actuator are pivotally mounted on a housing from a common second pivot point, wherein the linkage links the piston actuator in rotation when the user operated handle is released to unload the first spring.

* * * * *